United States Patent [19]
Healy et al.

[11] Patent Number: 5,863,650
[45] Date of Patent: Jan. 26, 1999

[54] INTERFACIAL COATINGS

[75] Inventors: Kevin E. Healy, Evanston, Ill.; Jane P. Bearinger, Livermore, Calif.

[73] Assignee: BioEngineered Materials, Inc., Evanston, Ill.

[21] Appl. No.: 851,197

[22] Filed: May 5, 1997

[51] Int. Cl.⁶ .................................................. B32B 27/30
[52] U.S. Cl. .................. 428/336; 427/2.11; 427/2.12; 427/301; 427/387; 427/407.1; 427/512; 428/216; 428/448; 428/451; 428/520; 428/522
[58] Field of Search ...................................... 428/213, 215, 428/216, 336, 448, 451, 520, 522; 427/2.1, 2.11, 2.12, 301, 387, 407.1, 512

[56] References Cited

U.S. PATENT DOCUMENTS 5,603,991  2/1997  Kupiecki et al. ....................... 427/508

*Primary Examiner*—D. S. Nakarani
*Attorney, Agent, or Firm*—Schiff Hardin & Waite

[57] ABSTRACT

An biologically compatible coating, enables an apparatus to which it is applied to resist to cell adhesion and/or protein adsorption. The coating comprises a polyacrylamide network grafted to a surface of the apparatus at polymerization sites on that surface and a poly(ethylene glycol) network interpenetrating the polyacrylamide network, and is prepared by sequentially polymerizing the polyacrylamide and poly(ethylene glycol) layers.

18 Claims, No Drawings

INTERFACIAL COATINGS

INTERFACIAL COATINGS

The present invention relates to the field of coatings for apparatus that are used as medical devices, for biotechnology applications, in pharmaceutical manufacture and processing, as biosensors, and other apparatus that may become fouled when proteins from blood, body fluids, or tissue are adsorbed on the surface of the apparatus. Such apparatus may be made from glass, ceramic, metal, or polymers such as polyethylene terephthalate. Protein deposition on the surface of an apparatus may leads to platelet, cell, and/or bacterial adhesion to the surface of the apparatus, potentially creating undesirable health hazards.

The invention seeks to overcome such problems by providing a surface coating for such apparatus that prevents or minimizes protein adsorption, and subsequent cell or bacterial adhesion, on the apparatus.

BACKGROUND OF THE INVENTION

Prior efforts to create coatings having such properties have focused upon the use of biologically compatible coatings that are grafted onto the surface of an apparatus. Such polymers include polyacrylamide and poly(ethylene glycol). Polyacrylamide has been grafted onto substrates using photoinduced polymerization, while poly(ethylene glycol) has been chemisorbed onto gold surfaces, centrifugally cast from a polymer mixture into vascular conduits, and gamma-irradiated onto silane-treated glass, among other methods.

Some methods of treating apparatus with biologically compatible coatings are disclosed in U.S. Pat. Nos. 4,722,906; 4,973,493; 4,979,959; 5,002,582; 5,091,205; 5,217,492; 5,258,041; 5,263,992; and 5,414,075.

These prior methods for treating such apparatus to provide biologically compatible coatings have several demonstrated problems. First, the polymers fail to adhere to the substrate with enough strength or resistance to wear. The polymers also may not exhibit consistent molecular structure. The density of the biocompatible polymer on the surface of the apparatus also may be insufficient to provide the desired resistance to cell adhesion or protein adsorption. Indeed, the art has been unable to achieve both sufficient chain density and poly(ethylene glycol) polymer chain length to create a coating having the desired level of resistance to cell and bacterial adhesion and/or protein adsorption for extended periods of time in challenging environments.

SUMMARY OF THE INVENTION

The present invention seeks to overcome such problems by providing an apparatus with a biologically compatible coating, resistant to cell adhesion and/or protein adsorption, that comprises a cross-linked polyacrylamide network grafted to a surface of the apparatus at polymerization sites on that surface and a sequential poly(ethylene glycol) network interpenetrating the polyacrylamide network.

According to the present invention, an apparatus is provided with a biologically compatible coating, resistant to cell adhesion and/or protein adsorption, by providing an apparatus to be coated that has polymerization sites on a surface of the apparatus; immersing the apparatus in a solution of acrylamide monomer, at least one photoinitiator, and at least one cross-linking agent; exposing the apparatus and solution to radiation to form a cross-linked polyacrylamide layer on the apparatus; immersing the apparatus in a solution of polyethylene glycol monomethyl ether monomethacrylate monomer, at least one photoinitiator, and at least one cross-linking agent; exposing the apparatus and poly(ethylene glycol) solution to radiation to form an interpenetrating network of poly(ethylene glycol) and polyacrylamide on the surface of the apparatus; and drying the coated apparatus.

It is an object of the present invention to provide a biologically compatible coating for an apparatus that exhibits superior resistance to protein adsorption and cell adhesion than earlier coatings.

It is another object of the invention to provide a coating that forms a thin layer that conforms to the surface of an apparatus, such that bulk performance properties (such as mechanical, electrical or optical properties) are maintained.

Another object of the invention is to achieve the desired level of resistance to cell adhesion and protein adsorption by providing an interpenetrating polymer network of polyacrylamide and poly(ethylene glycol) that maximizes the density of poly(ethylene glycol) chains without unduly restricting the poly(ethylene glycol) chain length.

Still another object of the invention is to provide such a coating that can be used on apparatus prepared from materials that include unsaturated bonds at the surface of the apparatus as well as apparatus that do not contain such unsaturated bonds at the surface.

These and other objects of the invention are described below.

DETAILED DESCRIPTION OF AN EMBODIMENT

The invention is found in an interfacial coating that can be applied to any number of apparatus that are contacted by biological materials such as blood, body fluids, proteinaceous solutions, and living tissue. Such apparatus include angioplasty balloon catheters, stents, vena cava filters, reaction vessels, and the like, and may be made from a polymer, from glass, from ceramic, or from a coated or uncoated metal such as stainless steel or titanium.

The surface of the apparatus first must be prepared to receive the interfacial coating. This is accomplished by locating sites on the surface of the apparatus at which photoinitiated polymerization can occur; these can include sites at which unsaturated bonds are present, either in the material from which the apparatus is constructed or as a result of the application of an initial coating (such as an organosilane) as described below.

If the apparatus requires the addition of a surface layer of a material containing polymerization sites before coating, the apparatus may be cleaned with an oxygen plasma or an argon plasma to provide an oxidized surface. For example, an apparatus having a polyethylene or polyethylene terephthalate surface may be exposed to an argon or oxygen plasma according to known methods, such as those disclosed in M. Suzuki et al., "Graft Copolymerization of Acrylamide onto a Polyethylene Surface Pretreated with a Glow Discharge," 1986 *Macromolecule* v. 19 at 1804–08 (1986). This introduces free hydrogen or peroxide groups onto the surface, which are amenable to hydrogen abstraction by benzophenone or its water-soluble equivalents. Alternatively, an apparatus made from a polymer such as poly(dimethylsiloxane) can be exposed to an oxygen plasma to introduce a thin $SiO_x$ oxide on the surface, which then is amendable to coupling an organosilane.

The apparatus with an oxide (either native or introduced) then is dip coated in an organosilane solution to provide a monolayer of unsaturated sites at the surface, thereby providing the homogeneity and density of polymerization sites needed to form a suitable interfacial coating. Suitable organosilane solutions include: 1% (v/v) allyltrichlorosilane in anhydrous toluene; 1% (v/v) 3-acryloxypropyltrimethoxysilane in 6 ml acetic acid/94 ml anhydrous methanol; and 1% (v/v) 7-octenyltrimethoxysilane in 6 ml acetic acid/94 ml anhydrous methanol. The apparatus must be immersed in the solution for a time sufficient to permit the organosilane solution to be adsorbed onto the surface of the apparatus; this typically is 15–60 seconds, depending upon the concentration and other characteristics of the organosilane solutions and the characteristics of the apparatus. Following immersion in the organosilane solution, the apparatus is rinsed in a suitable solvent (such as methanol or acetone), to remove excess organosilane solution, and dried to couple the silane to the surface. The details of the drying step will vary with the thermal properties of the base material, but will readily be determined and understood by those skilled in the art.

In still another method of surface preparation, the apparatus includes a surface polymer that swells when exposed to a solution that includes the cross-linking agent and acrylamide monomer as described below. The surface is treated with such a solution, and then rinsed in a non-solvent for the surface polymer so that the surface polymer does not swell or dissolve. See N. P. Desai et al, "Solution Technique to Incorporate Polyethylene Oxide and Other Water-Soluble Polymers into Surfaces of Polymeric Biomaterials," 1991 *Biomaterials* v. 12 at 144 et seq. (1991). For example, a polyethylene terephthalate surface may be exposed to a solution of 20% water and 80% trifluoroacetic acid, along with acrylamide monomer and cross-linker, and then rinsed in water or heptane to entrap the monomer and cross-linking agent in the surface polymer. This leaves the surface with acrylamide monomer and cross-linking agent presented at the surface to provide sites for polymerization.

The density and homogeneous distribution of such sites on the surface of the apparatus must be sufficient to permit a complete and generally even coating over the surface of apparatus. The increased density of such coatings leads to superior resistance to cell adhesion and protein adsorption, improving the performance of the apparatus coated according to the invention.

After the surface is prepared with polymerization sites, a network of polyacrylamide is formed on the surface of the apparatus, with or without the organosilane layer. The polyacrylamide layer is then added to the apparatus by immersing the prepared apparatus in a bath containing a solution of acrylamide. The solution may be in acetone, methanol, water, or a mixture of acetone and water. The solution also contains a cross-linking agent, such as N,N-methylene-bis-acrylamide, poly(ethylene glycol) dimethacrylate, poly(ethylene glycol) diacrylate, or poly(ethylene glycol) diglycidyl ether, and photoinitiators, such as camphorquinone, benzophenone (which is preferred), and (4-benzoyl benzyl) trimethyl ammonium chloride to initiate polymerization. The concentration of monomer and cross-linking agent should be high enough to form a very thin (about 20–30 nm), highly cross-linked hydrogel at the surface of the apparatus and to achieve a continuous coating at the interface of the apparatus and the fluids or materials that the apparatus will contact. For example, the concentration of monomer in solution may be from about 5–20% (w/v) (preferably about 5%), with a ratio of preferably from about 1–7% by weight cross-linking agent to total monomer. Prior to initiating polymerization, the solution is deoxygenated, preferably by bubbling nitrogen through the solution for 15–60 minutes. This also provides time for the monomer to be adsorbed to the surface of the apparatus.

The bath containing the monomer solution is retained in a light box or other suitable container for photoinitiation of the polymerization reaction of acrylamide. The polymerization reaction is triggered by exposing the solution containing the apparatus to ultraviolet radiation for a sufficient time to permit the solution to become viscous (but not gelatinous), typically from 30 seconds to 5 minutes, and preferably about 1.5 minutes, when the ambient temperature is about 70° C. The apparatus then is removed from the solution, and excess polymer is rinsed off in a suitable solvent, such as acetone, under ultrasonic agitation.

Following addition of the polyacrylamide layer, a network of poly(ethylene glycol) is formed on the apparatus to interpenetrate the polyacrylamide layer. The polymerization process is repeated in a solution containing polyethylene glycol monomethyl ether monomethacrylate monomers (preferably having a molecular weight of about 200–5000), cross-linking agents such as those disclosed above, and photoinitiators. The concentration of monomer in this solution is from about 5–20% (w/v), with a ratio of from about 5–70% by weight cross-linking agent to total monomer. Other acrylate- and methacrylate-based monomers can be used in place of polyethylene glycol monomethyl ether monomethacrylate without departing from the invention. The solvent used is methanol, which produces a superior interpenetrating network as compared with an acetone solution because it causes greater swelling of the polyacrylamide layer. Polymerization is photoinitiated as above until the solution becomes viscous (preferably, about 5 minutes using camphorquinone as the photoinitiator and methanol as the solvent), and the apparatus then is removed from solution. The poly(ethylene glycol) network so formed interpenetrates the polyacrylamide network formed during the first polymerization, producing a tightly bound surface that resists adsorption of proteins and, concomitantly, cell and bacterial adhesion.

The apparatus then is removed from the poly(ethylene glycol) solution and rinsed in a suitable solvent, such as methanol or water, to remove excess polymer. Finally, the coated apparatus is air dried, though other suitable drying methods can be used.

The thickness of the coating so formed can be controlled by adjusting the concentration of monomer and cross-linking agent, and the other polymerization conditions. Suitable coating thickness may be determined by the conditions under which the apparatus will operate and the materials that the apparatus will contact, and will be generally understood by those skilled in the field. Typical coatings formed according to the invention will include a polyacrylamide layer about 150 Å thick, and a poly(ethylene glycol) layer at least 50 Å thick.

What follows is an example of the application of the invention to a particular embodiment. Silicon and quartz discs were used as model metal oxide surfaces. The disks were exposed to an oxygen plasma environment to clean their surfaces, and then soaked in a 1.25 v/v % allyltrichlorosilane solution in anhydrous toluene. Acrylamide then was grafted onto the silane layer by photoinitiated synthesis using camphorquinone and N,N-methylene-bis-acrylamide as a cross-linking agent. A copolymer interpenetrating network was created by further photoinitiated synthesis of polyethylene glycol monomethyl ether monomethacrylate (MW 1000) within the acrylamide layer, also using camphorquinone and N,N-methylene-bis-acrylamide. The discs so treated showed substantial improvement in wettability and in resistance to protein adsorption and substantially reduced cell and bacterial adhesion.

The invention thus provides a coating for apparatus that exhibits superior graft strength using an interpenetrating polymer network providing superior strength as compared with conventional coatings. In addition, the interpenetrating network permits a greater surface density of poly(ethylene glycol) chains, enhancing the coating's resistance to protein adsorption and cell adhesion as compared with the prior art.

The present invention has been described with respect to certain embodiments and conditions which are not meant to and should not be construed to limit the scope of the invention. Those skilled in the art will understand that variations from the embodiments and conditions described herein may be made without departing from the invention as defined in the appended claims.

What is claimed is:

1. A biologically compatible coating, resistant to cell adhesion and/or protein adsorption, for an apparatus, comprising:
   a cross-linked polyacrylamide network grafted to a surface of the apparatus at polymerization sites on that surface;
   a sequential poly(ethylene glycol) network interpenetrating the polyacrylamide network.

2. The coating of claim 1, further comprising an unsaturated organosilane layer adsorbed onto the surface of the apparatus for providing the polymerization sites.

3. The coating of claim 1, wherein the polyacrylamide network is about 150 Å thick.

4. The coating of claim 1, wherein the poly(ethylene glycol) network is about 50 Å thick.

5. A method for coating an apparatus with a biologically compatible coating, resistant to cell adhesion and/or protein adsorption, comprising the steps of:
   providing an apparatus to be coated that has polymerization sites on a surface of the apparatus;
   immersing the apparatus in a solution of acrylamide monomer, at least one photoinitiator, and at least one cross-linking agent;
   exposing the apparatus and solution to radiation to form a polyacrylamide layer on the apparatus;
   immersing the apparatus in a solution of polyethylene glycol monomethyl ether monomethacrylate monomer, at least one photoinitiator, and at least one cross-linking agent;
   exposing the apparatus and poly(ethylene glycol) solution to radiation to form an interpenetrating network of poly(ethylene glycol) and polyacrylamide on the surface of the apparatus;
   and drying the coated apparatus.

6. The method of claim 5, wherein the polymerization sites are provided by coating the apparatus with an unsaturated organosilane.

7. The method of claim 6, wherein the surface is prepared to receive the unsaturated organosilane by exposing the apparatus to an oxygen plasma to oxidize the surface of the apparatus.

8. The method of claim 5, wherein the surface is prepared to receive the unsaturated organosilane by exposing the apparatus to argon plasma to oxidize the surface of the apparatus.

9. The method of claim 5, wherein the polymerization sites are provided by swelling the surface in a solution of acrylamide monomer and at least one cross-linking agent to entrap the acrylamide monomer and cross-linking agent within the surface.

10. The method of claim 5, wherein the photoinitiator is selected from the group consisting of camphorquinone benzophenone, and (4-benzoyl benzyl) trimethyl ammonium chloride.

11. The method of claim 5, wherein the cross-linking agent is selected from the group consisting of N,N-methylene-bis-acrylamide, poly(ethylene glycol) dimethacrylate, poly(ethylene glycol) diacrylate, and poly (ethylene glycol) diglycidyl ether.

12. An biologically-compatible coated apparatus resistant to cell adhesion and/or protein adsorption, made according to the steps of:
   providing an apparatus to be coated that has polymerization sites on a surface of the apparatus;
   immersing the apparatus in a solution of acrylamide monomer, at least one photoinitiator, and at least one cross-linking agent;
   exposing the apparatus and solution to radiation to form a polyacrylamide layer on the apparatus;
   immersing the apparatus in a solution of polyethylene glycol monomethyl ether monomethacrylate monomer, at least one photoinitiator, and at least one cross-linking agent;
   exposing the apparatus and poly(ethylene glycol) solution to radiation to form an interpenetrating network of poly(ethylene glycol) and polyacrylamide on the surface of the apparatus;
   and drying the coated apparatus.

13. The apparatus of claim 11, wherein the polymerization sites are provided by coating the apparatus with an unsaturated organosilane.

14. The apparatus of claim 11, wherein the surface is prepared to receive the unsaturated organosilane by exposing the apparatus to an oxygen plasma to oxidize the surface of the apparatus.

15. The apparatus of claim 11, wherein the surface is prepared to receive the unsaturated organosilane by exposing the apparatus to argon plasma to oxidize the surface of the apparatus.

16. The apparatus of claim 11, wherein the polymerization sites are provided by swelling the surface in a solution of acrylamide monomer and at least one cross-linking agent to entrap the acrylamide monomer and cross-linking agent within the surface.

17. The apparatus of claim 11, wherein the photoinitiator is selected from the group consisting of camphorquinone, benzophenone, and (4-benzoyl benzyl) trimethyl ammonium chloride.

18. The apparatus of claim 11, wherein the cross-linking agent is selected from the group consisting of N,N-methylene-bis-acrylamide, poly(ethylene glycol) dimethacrylate, poly(ethylene glycol) diacrylate, and poly (ethylene glycol) diglycidyl ether.

\* \* \* \* \*